United States Patent [19]

Huntoon et al.

[11] Patent Number: 4,834,733
[45] Date of Patent: May 30, 1989

[54] FLUID ACTIVATED MECHANICAL ABSORBENCY GAUGE

[75] Inventors: Andrew E. Huntoon, Appleton; Thomas H. Roessler, Menasha, both of Wis.

[73] Assignee: Kimberly-Clark Corporation, Neenah, Wis.

[21] Appl. No.: 119,598

[22] Filed: Nov. 12, 1987

[51] Int. Cl.⁴ .................. A61F 13/16; G01N 5/02
[52] U.S. Cl. .............................. 604/361; 73/73
[58] Field of Search ................. 604/361; 73/73; 116/200, 206, 211, 278, 335

[56] References Cited

U.S. PATENT DOCUMENTS

| | | | |
|---|---|---|---|
| 1,137,795 | 5/1915 | Schweiger | 73/73 |
| 1,773,114 | 8/1930 | Mueller | 73/73 |
| 2,681,032 | 6/1954 | Shaw | 604/361 |
| 2,929,241 | 3/1960 | Gebhart | 73/73 |
| 3,019,638 | 2/1962 | Klein | 73/73 |
| 3,139,854 | 7/1964 | Hedges et al. | 116/278 |
| 4,022,211 | 5/1977 | Timmons et al. | 604/361 |
| 4,357,938 | 11/1982 | Ito et al. | 604/376 |
| 4,447,240 | 5/1984 | Ito et al. | 604/385 |
| 4,484,573 | 11/1984 | Yoo | 128/138 A |
| 4,623,342 | 1/1986 | Ito et al. | 604/385 A |

FOREIGN PATENT DOCUMENTS

| | | | |
|---|---|---|---|
| 2031104 | 12/1971 | Fed. Rep. of Germany | 604/361 |
| 2183160A | 6/1987 | United Kingdom | 604/361 |

Primary Examiner—C. Fred Rosenbaum
Assistant Examiner—Sharon Rose
Attorney, Agent, or Firm—Paul Yee

[57] ABSTRACT

A distinctive absorbent article includes a backsheet layer and an absorbent body superposed in adjacent, facing relation with the backsheet layer. An actuating member connects to the article in liquid communication with the absorbent body and is composed of a liquid-contractible material. The liquid-contractible material is capable of shrinking upon contact with an aqueous liquid while maintaining a substantially unitary configuration. An indicating mechanism is connected to the actuating member for designating a wetness condition of the absorbent body, and is translatable along a selected path in response to the shrinkage of the actuating member.

24 Claims, 5 Drawing Sheets

FLUID ACTIVATED MECHANICAL ABSORBENCY GAUGE

Field of the Invention

The present invention relates to an absorbent article which includes an absorbency gauge therein. More particularly, the present invention relates to a mechanical gauge for indicating a relative amount of absorbed liquid within the article.

BACKGROUND OF THE INVENTION

Absorbent articles, such as diapers, incontinence garments and the like, are generally capable of absorbing multiple discharges of liquid from the wearer. As a result, the use condition of the absorbent article is not readily apparent from casual inspection. It has often been necessary to reach into the garment or open the garment to touch and feel the degree of dampness therein. This task may be unpleasant. In addition, the article may contain superabsorbent materials, which efficiently hold liquids, but may obscure the feeling of dampness within the absorbent article. Because of the difficulty in gauging the dampness condition of the article, the article may be left on the wearer for too long a time period. The absorbent capacity of the article may be exceeded and the skin of the wearer may become overly hydrated. As a result, the diaper may leak and become discomforting to the wearer.

Certain attempts have been made to provide a device for indicating the degree of wetness within a diaper. For example, U.S. Pat. No. 2,681,032 issued June 15, 1954 to J. Shaw describes a diaper which includes a device for indicating a condition of dampness therein. The device comprises a stretched resilient member, such as a rubber band, connected with a frangible means which has so low a wet strength that it is broken by the contractile force stored up on the resilient member. The breaking of the frangible means allows the resilient member to contract and move an indicator into a portion where it can be viewed.

U.S. Pat. No. 4,022,211 issued May 10, 1977 to T. Timmons, et al. describes a wetness indicator which employs a water-dispersible dye printed in a selected pattern onto an absorbent article. A disappearance of the dye pattern indicates the presence of water within the article. Other types of dye indicators employ liquid-activated dyes which become visible when wetted.

Another type of detection device is described in U.S. Pat. No. 4,484,573 issued Nov. 27, 1984 to K. Yoo. This device employs an electronic alarm mechanism to detect moisture within a diaper.

Liquid-contractible elastic materials have been known in the art and have been employed to elasticize particular portions of a disposable diaper. For example, U.S. Pat. No. 4,357,938 issued Nov. 9, 1982 to O. Ito, et al. describes a disposable diaper comprising a water-absorbing layer located between a liquid-permeable surface sheet and a liquid-impermeable backing sheet. A means is provided so that the water-absorbing shrinkable fibers become wetted when the diaper is wetted and thereby shrink to elasticize the diaper edge. Similarly, U.S. Pat. No. 4,623,342 issued Nov. 18, 1986 to Ito, et al. describes a disposable diaper having water-absorptive, shrinkable fiber strings to form gaskets against the legs and thighs of the wearer.

Conventional dampness indicators, however, have not been sufficiently able to gauge the dampness condition within an absorbent garment, and have not provided an adequate signal of the appropriate time to change the garment. As a result, the garment may be left on the wearer for too long a period thereby allowing leakage of fluids from the diaper and causing discomfort to the wearer.

BRIEF DESCRIPTION OF THE INVENTION

The present invention provides a distinct absorbent article which includes a backsheet layer, and an absorbent body superposed in adjacent, facing relation with the backsheet layer. An actuating member is connected to the article in liquid communication with the absorbent body and is composed of a liquid-contractible material. The liquid-contractible material is capable of shrinking upon contact with water while maintaining a substantially unitary configuration. An indicating means is connected to the actuating member for designating a wetness condition of the absorbent body, and is translatable along a selected path in response to the shrinkage of the actuating member.

In a particular aspect of the invention, the absorbent article comprises an absorbent body having lateral side edges, and a substantially liquid-impermeable backsheet layer superposed in facing relation with the absorbent body. A gatherable gasket member extends from each of the lateral side edges of the absorbent body, and an elastic member is connected to each of the gatherable gasket members for shirring the gasket members. An actuating member is connected to the article in liquid communication with the absorbent body, and is composed of a liquid-contractible material, which is capable of shrinking upon contact with water or other aqueous liquid. An indicating means is connected to the actuating member for designating a wetness condition of the absorbent body. The indicating means comprises portion of the article attached to the actuating member at discrete, spaced apart sections thereof. The attached portion of the article is arranged to form corrugations therein in response to the shrinkage of the actuating member.

The present invention can advantageously help the consumer use the absorbent article with more optimum effectiveness. For example, the invention can alert the consumer when the maximum fluid-holding capacity of the garment is being reached. In addition, the invention can more effectively alert and direct a consumer to change the article before excessive wetness develops against the wearer's skin and before an oversaturation of the article induces undesired leakage. Particular aspects of the invention can also provide incremental indications of the degree of saturation of the absorbent article, or of the degree of wetness present at a bodyside liner layer of the article.

BRIEF DESCRIPTION OF THE DRAWINGS

The present invention will be more fully understood and further advantages will become apparent when reference is made to the following detailed description of the invention and the drawings, in which:

FIG. 8 representatively shows a plot of the mechanical absorbency gauge movement as a function of the amount of synthetic urine add-on.

DESCRIPTION OF THE INVENTION

The following description of the invention will be made in the context of a disposable diaper. It will be readily apparent, however, that the invention can be readily adapted for use in other absorbent articles, such as incontinence garments, training pants or the like. While the following description is made in the context of a diaper having a single absorbency gauge therein, it is contemplated that other embodiments of the invention may include a plurality of absorbency gauges placed at different selected locations within an absorbent article. Such a configuration could be employed to give separate indications of the amount of absorbent capacity remaining in different portions of the article.

Figure 1:
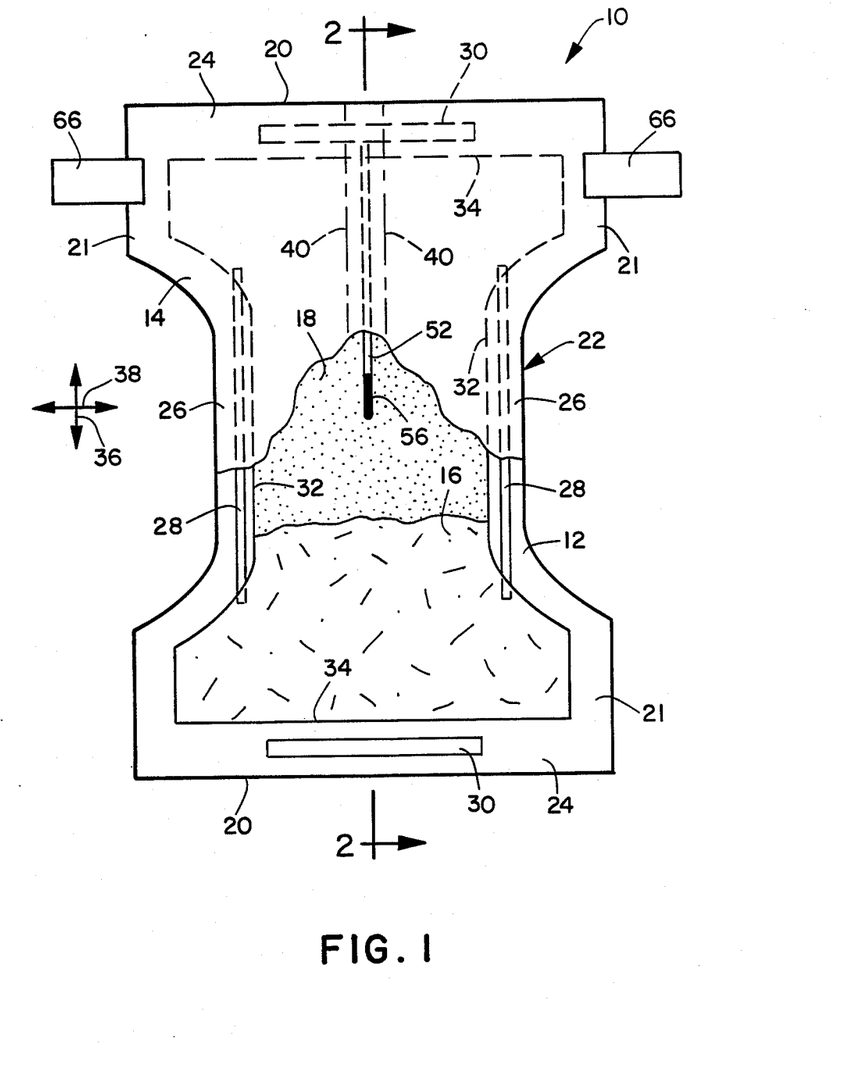
FIG. 1 representatively shows a schematic, cut-away plan view of a disposable diaper incorporating the absorbency gauge of the present invention.

With reference to FIG. 1, a representative absorbent article, such as diaper 10, typically includes a backsheet layer 14 and an absorbent body 16 superposed in adjacent, facing relation with the backsheet layer. An actuating member, such as actuating strand 52, is connected to diaper 10 in liquid communication with absorbent body 16, and is composed of a liquid-contractible material. The liquid-contractible material is capable of shrinking upon contact with water while maintaining a substantially unitary configuration. The actuating member advantageously does not require a component which must fracture or break before the actuating member is capable of contracting. Neither is the actuating member under a continuous mechanical stress which might prematurely activate the device and provide a false reading. The liquid-contractible material is capable of shrinking in a plurality of increments which are generally proportional to a degree of contact with the aqueous liquid encountered by the actuating member. An indicating means, such as indicator tab portion 56, is connected to the actuating member and is arranged to designate a wetness condition of the absorbent body. The indicating means is translatable along a selected path in response to the shrinkage of actuating strand 52.

Figure 5:
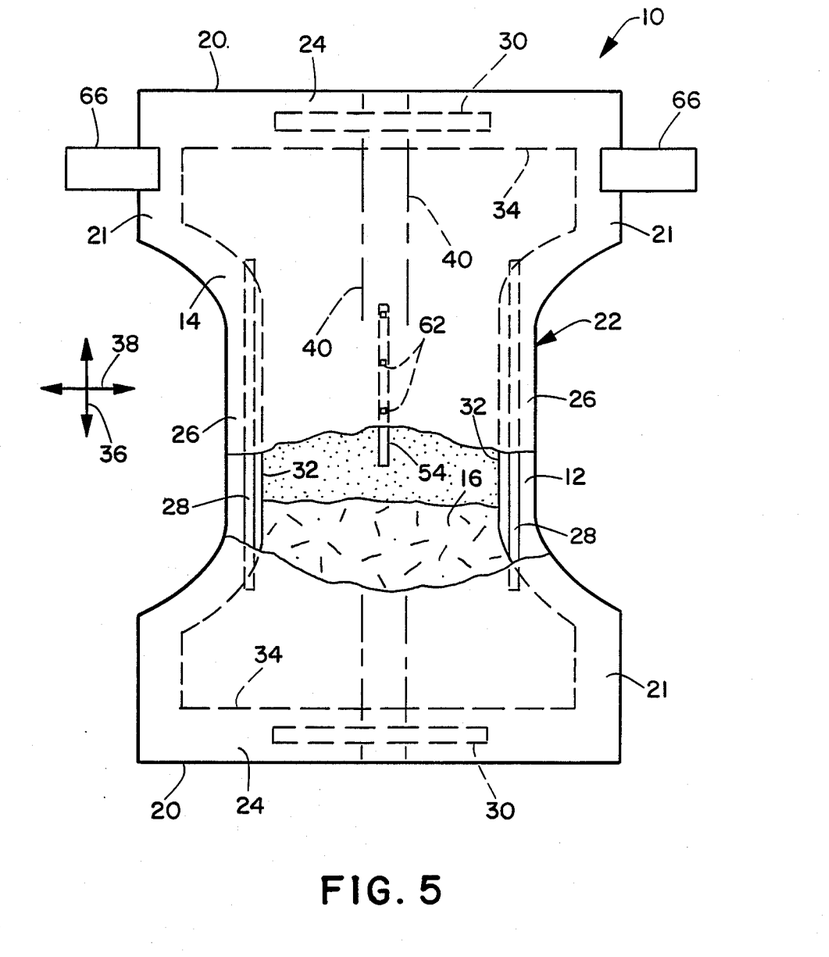
FIG. 5 representatively shows a plan view of an embodiment of the invention wherein the wetness indication is signaled by a selected gathering or corrugation of a component layer of the diaper.

In a particular aspect of the invention representatively shown in FIG. 5, an absorbent article, such as diaper 10, includes an absorbent body 16 having lateral side edges 32. A substantially liquid-impermeable backsheet layer 14 is superposed in facing relation with the absorbent body, and a gatherable gasket member 26 extends from each of the lateral side edges of absorbent body 16. A leg elastic member 28 is connected to each of the gatherable gasket members 26 and is arranged to shirr the gasket member. An actuating member, such as actuating strip 54, is connected to diaper 10 in liquid communication with absorbent body 16 and is composed of a liquid-contractible material which is capable of shrinking upon contact with an aqueous liquid. An indicating means is connected to actuating strip 54 for designating a wetness condition of absorbent body 16. The indicating means comprises a portion of diaper 10 which is attached to actuating strip 54 at discrete, spaced apart sections thereof. The attached portions of diaper 10 are arranged to form corrugations therein in response to the shrinkage of actuating strip 54.

Referring again to FIGS. 1 and 2, a representative diaper 10 typically includes a topsheet layer 12, a backsheet layer 14 and an absorbent body 16 sandwiched between the topsheet and backsheet layers. Absorbent body 16 is ordinarily smaller than backsheet 14 and topsheet 12 with the topsheet and backsheet extending past the end edges 34 of absorbent body 16 to form end margins 24. A gatherable gasket member 26 extends laterally from each lateral side edge of absorbent body 16. In the illustrated embodiment, gasket member 26 comprises those side marginal portions of topsheet 12 and backsheet 14 which extend laterally past the side edges 32 of the absorbent body. Alternatively, gasket member 26 may comprise a distinct, separate element connected to either or both of the topsheet and backsheet layers. Leg elastic members 28 connect to each of the gasket members and are suitably arranged to gather and shirr the gasket member to provide resilient seals about the legs of the wearer.

Diaper 10 may have various shapes and configurations. For example, the diaper may have a generally rectangular planform or may have a T-shaped planform. In the illustrated embodiment, diaper 10 is approximately hourglass-shaped or I-shaped and generally defines two waistband sections 20 interconnected by an intermediate section 22. The waistband sections each define ear sections 21 which extend oppositely along the lateral cross-direction 38 of the diaper. Two ear sections at one waistband portion of the diaper include securement means for fastening the diaper on the wearer. In the shown embodiment, the securement means are operably connected to the ear sections of the rear waistband portion of the diaper, and comprise pressure-sensitive adhesive tape tabs 66. It is readily apparent, however, that various other securement means, such as hooks, snaps, hook and loop fasteners, mushroom and loop fasteners, cohesive strips and the like could also be employed. Diaper 10 may also include waist elastic members 30 secured to one or more of the diaper end margins 24 to gather and shirr the waistbands of the diaper. The intermediate section of diaper 10 is intended for placement between the legs in the crotch region of the wearer, and the waistband sections are placed against the wearer's front and back to encircle the waist.

The various components of diaper 10 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by conventional techniques, such as by spraying droplets or filaments of the adhesive. In the shown embodiment, the components are assembled employing a plurality of generally parallel lines of hot melt pressure-sensitive adhesive aligned along the length dimension 36 of the diaper. The adhesive lines are configured and arranged to bond the backsheet and topsheet to the absorbent body, and bond the marginal side and end portions of the topsheet to the corresponding, adjacent marginal portions of the backsheet.

In the illustrated embodiment of the invention, diaper 10 includes a backsheet composed of a liquid-impermeable, substantially inelastic material, such as a polymer film. For example, backsheet 14 can be composed of a polyolefin film, such as polyethylene or polypropylene. In another embodiment of the invention, backsheet 14 can be composed of a liquid-impermeable but vapor-permeable material, such as a "breathable" microporous polyethylene film. The polymer film comprising backsheet 14 typically has a thickness within the (L range of about 0.0005–0.0020 inches. Preferably, however, the polymer film has a thickness within the range of about 0.0007–0.0015 inches.

Backsheet 14 may alternatively comprise a nonwoven fibrous web, such as a spunbond web or meltblown web, which has been suitably constructed and arranged to be substantially liquid-impermeable. The nonwoven fibrous web may also be constructed to be liquid-impermeable but vapor-permeable. For example, the nonwoven fibrous web may be combined with a selected coating or polymer film to impart a desired degree of liquid-impermeability and vapor-permeability. Typically, the nonwoven fibrous web has a basis weight within the range of about 0.9–2.5 oz/yd$^2$, and preferably has a basis weight within the range of about 1.3–1.7 oz/yd$^2$ provide improved comfort and effectiveness.

Topsheet 12 is typically composed of a liquid-permeable, substantially inelastic and substantially hydrophobic material, such as a spunbonded web composed of synthetic polymer filaments. Alternatively, topsheet 12 may comprise a meltblown web or a bonded-carded-web composed of synthetic polymer filaments. Suitable synthetic polymers include, for example, polyethylene, polypropylene and polyesters. The topsheet has a pore size that readily allows the passage therethrough of liquids, such as urine and other body exudates. Optionally, the topsheet can be treated with surfactants to selectively adjust its degree of wettability, and can also be selectively embossed or perforated to provide discrete slits or holes extending therethrough.

Absorbent body 16 typically comprises a pad composed of airlaid, cellulosic fibers commonly referred to as wood pulp fluff. Conventional pads can have a density ranging from about 0.05–0.20 g/cc, and are sufficiently flexible to readily conform to the body of the wearer. Absorbent body 16 may alternatively comprise a coform material composed of a mixture of cellulosic fibers and synthetic polymer fibers. For example, the coform material may comprise an airlaid blend of cellulosic fibers and meltblown polyolefin fibers, such as polyethylene and polypropylene fibers.

The absorbent body may also include an effective amount of an inorganic or organic high-absorbency material to enhance the absorptive capacity of the absorbent body. For example, absorbent body 16 can include 5–95 wt % high-absorbency material, and preferably includes about 10–30 wt % of the high-absorbency material to provide more efficient performance. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to render the materials substantially water-insoluble. The cross-linking may, for example, be by irradiation or by covalent, ionic, Van der Waals, or hydrogen bonding. Suitable materials are available from various commercial vendors, such as Dow Chemical Company, Celanese Corporation, Allied-Colloid, and Stockhausen. Typically, the high-absorbency material is capable of absorbing at least about 15 times its weight in simulated urine, and preferably is capable of absorbing at least about 25–50 times its weight in simulated urine.

The high-absorbency material can be distributed or otherwise incorporated into absorbent body 16 employing various techniques. For example, the high-absorbency material can be substantially uniformly distributed in the mass of fibers comprising the absorbent body. The material can also be nonuniformly distributed among the fibers to form a generally continuous gradient with either an increasing or decreasing concentration of high-absorbency material, as determined by observing the concentration moving from the bodyside of absorbent body 16 to the outerside of the absorbent body. Alternatively, the high-absorbency material can comprise a discrete layer separate from the fibrous material of absorbent body 16 or can comprise a discrete layer integral with the absorbent body.

Absorbent body 16 can optionally include a tissue wrap 18 to help maintain the integrity of the airlaid fibrous structure. The tissue wrap typically comprises a hydrophilic cellulosic material, such as creped wadding or a high wet-strength tissue, and may extend over either or both of the outerside and bodyside surfaces of the absorbent body.

The liquid-contractible material of the actuating member may comprise any moisture-activated, shrinkable material, such as rayon or cotton yarns. Preferably, however, the actuating member is composed of a high shrinkage yarn such as Vinylon-type yarns of Unitika Kasei, Ltd. of Osaka, Japan and Kuralon-type yarns of Mitsubishi International Corporation of Osaka, Japan. Such yarns are composed of synthetic fibers of polyvinyl alcohol.

The indicating means of the present invention may comprise any mechanism which can be mechanically activating by an applied tension. For example, the indicator can be as simple as a colored marker or tab which is attached to one end of the shrinkable actuating member. As the actuating member contracts, the indicator tab is displaced by a distance which can provide a visible measure of the level of detected dampness. The indicating means may also be a more complex mechanism which is activated by a particular level of tension within the actuating member. For example, the actuating member may be configured to operate a selected display mechanism, such as a dial, bar scale or a digital readout.

In a particular aspect of the invention, the indicating means provides a visual signal or display to the consumer through backsheet 14 or topsheet 12, as desired. When the display is visible through backsheet 14, the consumer may view the absorbency gauge without removing the diaper from the wearer. The consumer, however, may find it undesirable to have the absorbency gauge located at a readily visible portion of the diaper. Accordingly, the absorbency gauge may be positioned at a generally hidden location at the crotch region of the diaper, or may even be arranged such that the visual display is provided only through topsheet 12 of the diaper. With the latter configuration, it would be necessary to open the diaper to view the indicating means and read the absorbency gauge. Such incorporation of the absorbency gauge would still, however, allow the consumer to estimate the dampness condition within the diaper without actually touching any soiled materials.

Backsheet 14 or topsheet 12, whichever is appropriate, should be sufficiently transparent or translucent such that indicator tab 56 is readily visible through the material. Similarly, indicator tab 56 should be of suitable contrasting color to facilitate viewing through the backsheet or topsheet. The tab may be of any desired shape or form, but should offer little resistance to movement as the actuating member contracts and displaces the tab. For example, the indicator tab may be a segment of the actuating member itself which has been colored or which has been both shaped and colored. An arrangement wherein the indicator tab is simply a colored end of the actuating member would offer the minimum amount of resistance to displacement. Where the amount of discreteness is unimportant, the entire actuating member may be visibly colored.

Figure 2:
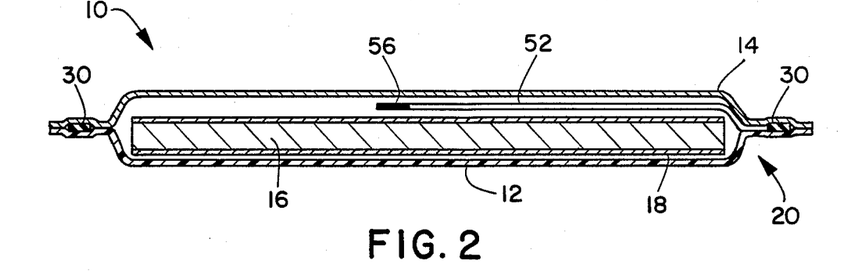
FIG. 2 representatively shows a schematic cross-sectional view taken along 2-2 of FIG. 1.

Referring to the embodiment representatively shown in FIGS. 1 and 2, the actuating member comprises a liquid-contractible strand 52, one end of which is connected to one waistband section of diaper 10. Strand 52 extends longitudinally along the length dimension of diaper 10 and is placed between backsheet and absorbent body 16. Alternatively, strand 52 may be placed between topsheet 12 and absorbent body 16. In either case, strand 52 is arranged to be in liquid communicative contact with the fluids discharged into absorbent body 16 to operably sense the wetness conditions therein.

Figure 3:
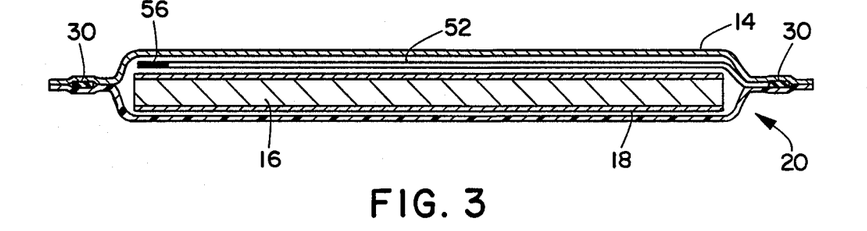
FIG. 3 representatively shows a cross-sectional view of an alternative embodiment of the invention.

Strand 52 may be arranged in various suitable configurations. For example, strand 52 may be affixed to one end of diaper 10 and extend approximately one-half of the diaper length to about the middle of the diaper intermediate section 22. Thusly configured, strand 52 would extend only to the crotch area of the wearer, and indicator tab 56 would be arranged to move from the diaper intermediate section toward the diaper waistband section upon the shrinkage and contraction of strand 52, as illustrated in FIG. 2. Alternatively, strand 52 may extend from one waistband section through the diaper intermediate section and into the opposite waistband section of the diaper. With this configuration, tab 56 would at least initially move in a direction away from the diaper waistband section and toward the diaper intermediate section 22, as illustrated in FIG. 3.

In a particular aspect of the invention, diaper 10 includes directing means for guiding the actuating member, or the indicating means or both along a selected movement path. The directing means may, for example, be selectively configured to guide strand 52 and indicator tab 56 along diaper length direction 36, diaper cross-direction 38 or along a combination of these two directions. In the illustrated embodiment, the directing means comprises two, generally parallel adhesive lines 40 which bond backsheet 14 to absorbent body 16 or to a layer of material positioned immediately adjacent to the inner, bodyside surface of the backsheet. Similarly, the directing means may comprise two, generally parallel lines which bond topsheet 12 to a layer of material immediately adjacent thereto. The placement of strand 52 and indicator tab 56 between the adhesive lines effectively constrains the lateral, side-to-side location and placement of the strand and tab, and reduces the chances that the ordinary handling of diaper 10 will displace the strand and tab away from the desired sensing position within the diaper. In addition, as strand 52 contracts upon exposure and contact with an aqueous liquid, the strand and indicator tab 56 are constrained to traverse along a predictable path that can be readily labelled with measuring means for gauging a relative amount of movement of tab 56 with respect to its initial starting position. The relative amount of movement of tab 56 can then be correlated with a wetness condition within absorbent body 16 and can thereby be employed to gauge the amounts of absorbent capacity remaining within the absorbent body.

Figure 4:
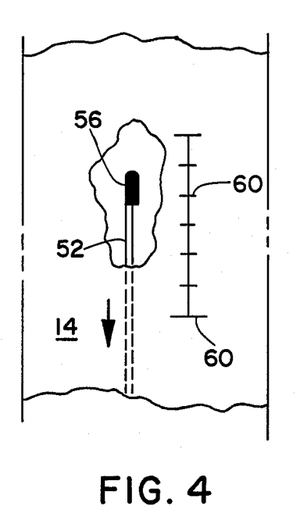
FIGS. 4 and 4A representatively show measurement means comprising selected patterns of markings for gauging a relative amount of wetness.
Figure 4A:
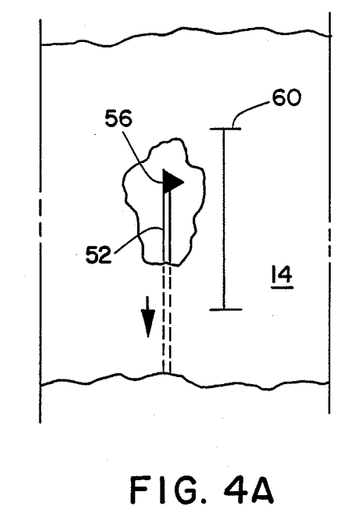

The measuring means may comprise any suitable indicia 60 against which to compare the movement and change of position exhibited by tab 56 under the influence of liquid-contractible strand 52. For example, the measuring means may comprise printed marking on the backsheet or topsheet, as appropriate. Alternatively, the measuring means may comprise a selected pattern of markings embossed onto the backsheet or topsheet. Preferably, the markings are substantially regularly spaced to provide an incremental gauge of the available absorbent capacity remaining in diaper 10, but irregularly spaced markings may also be employed.

Figure 6:
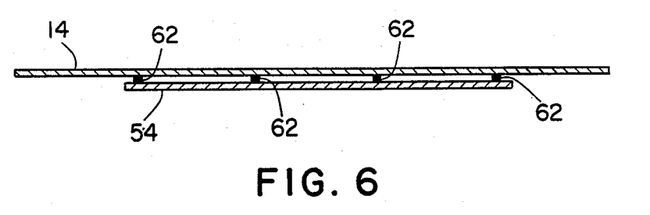
FIGS. 6 and 6A representatively show a cross-sectional view of the forming of corrugations in a selected layer of a diaper.
Figure 6A:
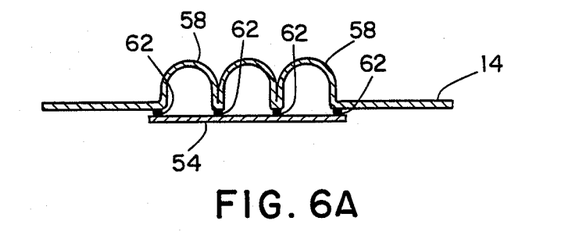

In a further embodiment of the invention, the absorbency gauge may be configured to provide a tactile indication of the wetness within diaper 10. For example, with reference to FIGS. 5, 6 and 6A, an actuating strip 54 is attached to the backsheet at spaced locations 62 along the strip. The spaced attachments are oriented along the length direction 36 of the diaper, and may comprise, for example, adhesive bonds, mechanical bonds, thermal bonds or the like. Upon exposure to water, strip 54 operably contracts and draws the attachment points 62 closer together. This action corrugates backsheet 14 and forms discrete pleats or gathers which protrude from the surrounding surface of the backsheet. Corrugations 58 are readily felt and perceived when touched by the consumer, and the degree of gathering and relative tactile roughness exhibited by corrugations 58 provides an indication of the amount of liquid already contained within the diaper.

While the actuating strip representatively shown in FIGS. 3 and 5 is aligned along the length direction of diaper 10, it will be readily apparent that strip 54 may alternatively be aligned along the diaper cross-direction 38. Similarly, strip 54 may alternatively be attached to another component layer of diaper 10, such as topsheet 12, to operably form corrugations 58 therein when strip 54 contracts upon exposure to water.

Figures 7, 7A:
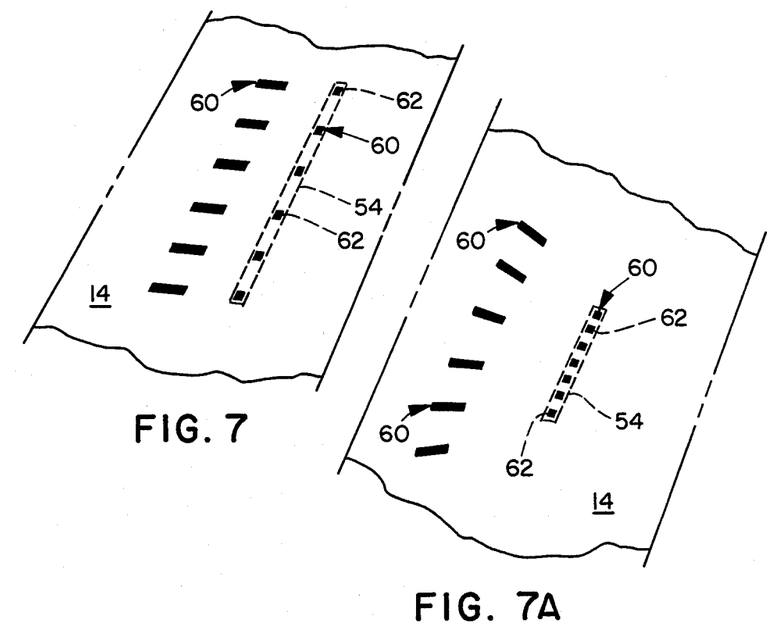
FIGS. 7 and 7A representatively show fractional views of an embodiment of the invention wherein the actuating member forms corrugations in the diaper backsheet and a selected pattern of markings is employed to gauge the relative amount of wetness.

In the above description, corrugations 58 have been described as providing a tactile output indication. It will be readily apparent, however, that the corrugations may also be configured to provide a visual signal display of the wetness condition within diaper 10. For example, the portion of the particular diaper layer, such as topsheet 12 or backsheet 14, to which strip 54 is attached may include a plurality of spaced markings arranged along the length direction of strip 54 in a selected pattern, as representatively shown in FIGS. 7 and 7A. The markings may, for example, be printed or embossed onto the selected diaper layer and may be regularly or irregularly spaced. Upon the contraction and shrinkage of strip 54, the sections of the markings located on corrugations 58 will translate and move closer together, or will otherwise create distortions of the original pattern of markings. This distortion can thereby provide a visible indication of the use condition of the diaper.

The following examples are provided to give a more detailed understanding of the invention. The particular materials, dimensions, amounts and other parameters are exemplary and are not intended to specifically limit the scope of the invention.

EXAMPLE

An absorbent diaper article was constructed to include a fluid activated mechanical absorbency gauge. The diaper comprises a backsheet layer composed of a 0.00128 inch thick polyethylene film having a titanium-oxide filler, and a substantially liquid-permeable topsheet layer composed of a spunbond, polypropylene fibrous web having a basis weight of about 0.75 oz/yd$^2$. An absorbent body was sandwiched between the backsheet and topsheet, and secured to the inner surface of the backsheet with a plurality of parallel lines of hot-melt adhesive (Findley 694-373B) with the adhesive lines spaced about 0.5 inches apart. The hotmelt adhesive lines also secured the marginal portions of the backsheet to the corresponding, adjacently located, marginal portions of the topsheet. The absorbent body had a density of about 0.12 g/cc, and was composed of about 80 wt % airlaid cellulosic fibers, about 11 wt % polyacrylate superabsorbent hydrogel, and about 9 wt % tissue wrap. An actuating member composed of a strand of moisture-shrinkable, polyvinyl alcohol yarn, was located between the backsheet and the absorbent body tissue wrap, and positioned between the two, centermost adhesive lines. One end of the actuating strand was secured to the backsheet near the back waistband edge of the absorbent body, and an indicator dot member was attached to the opposite, free end of the actuating strand.

Figure 8:
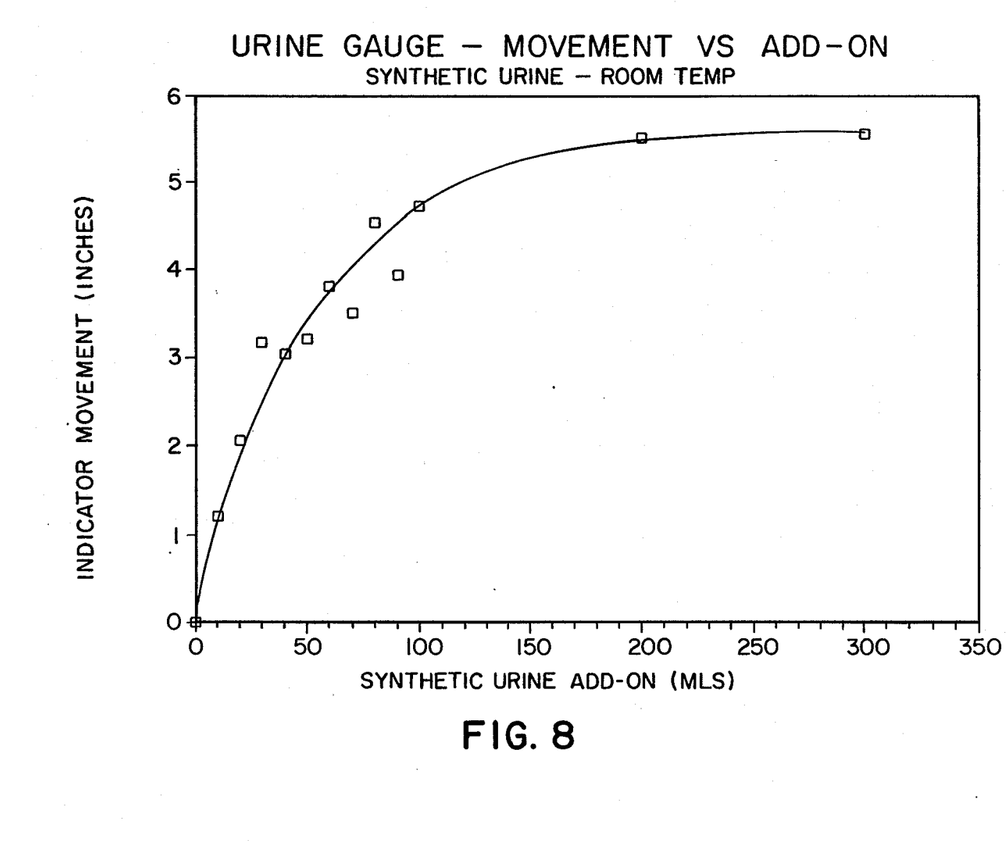

A number of diapers were constructed and loaded with varying amounts of synthetic urine solution. A representative plot of the mechanical absorbency gauge movement versus synthetic urine add-on is shown on the graph of FIG. 8.

Having thus describes the invention in rather full detail, it will be readily apparent to a person having ordinary skill in the art that various changes and modifications can be made without departing from the spirit of the invention. All of such changes and modifications are contemplated as being within the scope of the invention, as defined by the subjoined claims.

We claim:

1. An absorbent article comprising:
   a backsheet layer;
   an absorbent body superposed in adjacent, facing relation with said backsheet layer;
   an actuating member, which is connected to said article in liquid communication with said absorbent body and is composed or a liquid-contractible material, said liquid-contractible material capable of shrinking upon contact with an aqueous liquid while maintaining a substantially unitary configuration;
   an indicating means which is connected to said actuating member of designating a wetness condition of said absorbent body, and is translatable along a selected path in response to the shrinkage of said actuating member, said indicating means translatable in a plurality of increments which are correlated and generally proportional to a plurality of increasing levels of wetness in said absorbent body; and
   measurement means for gauging the levels of wetness of said absorbent body.

2. An absorbent article as recited in claim 1, wherein further comprising a liquid permeable topsheet layer positioned in superposed facing relation with said absorbent body to sandwich said absorbent body between said backsheet and topsheet layers.

3. An absorbent article as recited in claim 1, wherein said backsheet layer is composed of a material which is sufficiently transparent and wherein said indicator means is arranged to be operatively visible through said backsheet layer.

4. An absorbent article as recited in claim 1, wherein said backsheet layer is attached to said absorbent body with a plurality of generally parallel adhesive lines and wherein said indicator means is moveable along a path located between two adjacent adhesive lines.

5. An absorbent article as recited in claim 1, wherein said measurement means comprises one or more markings placed along a movement path of said indicating means.

6. An absorbent article as recited in claim 5, wherein said measurement means comprises a plurality of spaced markings.

7. An absorbent article as recited in claim 6, wherein said markings are substantially regularly spaced.

8. An absorbent article as recited in claim 8, further comprising directing means for guiding said indicating means along said selected path.

9. An absorbent article as recited in claim 8, wherein said directing means comprises two, generally parallel adhesive lines which bond said backsheet to said absorbent body and wherein said selected path lies between said adhesive lines.

10. An absorbent article comprising:
    a backsheet layer;
    an absorbent body superposed in adjacent, facing relation with said backsheet layer;
    an actuating member, which is connected to said article in liquid communication with said absorbent body and is composed of a liquid-contractible material, said liquid-contractible material capable of shrinking upon contact with an aqueous liquid while maintaining a substantially unitary configuration, and said actuating member not subject to a continuous mechanical stress arranged to break said actuating member before contraction thereof;
    an indicating means which is connected to said actuating member for designating a wetness condition of said absorbent body, and is translatable along a selected path in response to the shrinkage of said actuating member, said indicating means translatable in a plurality of increments which are correlated and generally proportional to a plurality of increasing levels of wetness in said absorbent body; and measurement means for gauging the levels of wetness of said absorbent body.

11. An absorbent article as recited in claim 10, wherein said indicating means comprises a portion of said article attached to said actuating member at discrete, spaced apart sections thereof.

12. An absorbent article as recited in claim 10, wherein further comprising a liquid permeable topsheet layer positioned in superposed, facing relation with said absorbent body to sandwich said absorbent body between said backsheet and topsheet layers.

13. An absorbent article as recited in claim 10, wherein said backsheet layer is composed of a material which is sufficiently transparent and wherein said indicator means is arranged to be operatively visible through said backsheet layer.

14. An absorbent article as recited in claim 10, wherein said backsheet layer is attached to said absorbent body with a plurality of generally parallel adhesive lines and wherein said indicator means is moveable along a path located between two adjacent adhesive lines.

15. An absorbent article as recited in claim 10, wherein said measurement means comprises one or more markings placed along a movement path of said indicating means.

16. An absorbent article as recited in claim 15, wherein said measurement means comprises a plurality of spaced markings.

17. An absorbent article as recited in claim 16, wherein said markings are substantially regularly spaced.

18. An absorbent article as recited in claim 10, further comprising directing means for guiding said indicating means along said selected path.

19. An absorbent article as recited in claim 18, wherein said directing means comprises two, generally parallel adhesive lines which bond said backsheet to said absorbent body and wherein said selected path lies between said adhesive lines.

20. An absorbent article, comprising:
an absorbent body having lateral side edges;
a substantially liquid-impermeable backsheet layer superposed in facing relation with said absorbent body;
a gatherable gasket member extending from each of the lateral side edges of said absorbent body;
an elastic member connected to each of the gatherable gasket members for shirring said gasket members;
an actuating member, which is connected to said article in liquid communication with said absorbent body and is composed of a liquid-contractible material, which is capable of shrinking upon the contact with an aqueous liquid;
indicating means connected to said actuating member for designating a wetness condition of said absorbent body, said indicating means comprising a portion of said article attached to said actuating member said attached portion of said article arranged to form corrugations therein in response to the shrinkage of said actuating member, said corrugations providing degrees of gathering correlated to a plurality of increasing amounts of wetness in said absorbent body; and
measurement means for gauging the degrees of gathering.

21. An absorbent article as recited in claim 20, wherein further comprising a liquid permeable topsheet layer positioned in superposed, facing relation with said absorbent body to sandwich said absorbent body between said backsheet and topsheet layers.

22. An absorbent article as recited in claim 20, wherein said measurement means comprises one or more markings placed along said portions of the article which are attached to said actuating member.

23. An absorbent article as recited in claim 22, wherein said measurement means comprises a plurality of spaced markings.

24. An absorbent article as recited in claim 23, wherein said markings are substantially regularly spaced.

* * * * *

UNITED STATES PATENT AND TRADEMARK OFFICE
CERTIFICATE OF CORRECTION

PATENT NO. : 4,834,733

DATED : May 30, 1989

INVENTOR(S) : Huntoon et al.

It is certified that error appears in the above-identified patent and that said Letters Patent is hereby corrected as shown below:

Column 2, Line 37, after the word "comprises" insert "a"

Column 5, Line 13, delete "(L"

IN THE CLAIMS:

Claim 1, Column 9, Line 66, delete "or" and substitute therefor -- of --

Claim 1, Column 10, Line 4, delete "of" and substitute therefor -- for --

Claim 8, Column 10, Line 39, delete "8" and substitute therefor -- 1 --

Signed and Sealed this

Twenty-first Day of May, 1991

Attest:

HARRY F. MANBECK, JR.

*Attesting Officer*  *Commissioner of Patents and Trademarks*